United States Patent
Centellas et al.

(10) Patent No.: US 6,949,519 B2
(45) Date of Patent: Sep. 27, 2005

(54) MACROLIDE SOLVATES

(75) Inventors: Victor Centellas, Cardedeu/Barcelona (ES); José Diago, Granollers/Barcelona (ES); Rafael Garcia, Sant Celoni/Barcelona (ES); Johannes Ludescher, Breitenbach (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/432,545

(22) PCT Filed: Nov. 26, 2001

(86) PCT No.: PCT/EP01/13760

§ 371 (c)(1),
(2), (4) Date: Oct. 10, 2003

(87) PCT Pub. No.: WO02/42315

PCT Pub. Date: May 30, 2002

(65) Prior Publication Data

US 2004/0053862 A1 Mar. 18, 2004

(30) Foreign Application Priority Data

Dec. 21, 2000 (GB) ............................................. 0031355

(51) Int. Cl.⁷ .............................................. C07H 17/05

(52) U.S. Cl. ........................... 514/29; 514/12; 514/152; 514/192; 514/927; 536/7.4; 536/18.5; 536/124; 424/451; 424/464

(58) Field of Search ........................ 514/29, 12, 152, 514/192, 927; 536/7.4, 18.5, 124; 424/451, 464

(56) References Cited

U.S. PATENT DOCUMENTS 6,268,489 B1   7/2001  Allen et al. ................... 536/7.4
6,703,372 B1 *  3/2004  Centellas et al. ............. 514/29

FOREIGN PATENT DOCUMENTS

| EP | 0 879 823 | 11/1998 |
| EP | 0 941 999 | 9/1999 |
| EP | 941 999 | * 9/1999 |
| EP | 0 984 020 | 3/2000 |
| EP | 1 103 558 | 5/2001 |
| WO | 01/00640 | 1/2001 |

\* cited by examiner

*Primary Examiner*—James O. Wilson
*Assistant Examiner*—Devesh Khare
(74) *Attorney, Agent, or Firm*—John D. Thallemer

(57) ABSTRACT

Azithromycin in the form of a monohydrate comprising from 4.0% to 6.5% of water, a process for its preparation and its use in pharmaceutical compositions.

7 Claims, No Drawings

MACROLIDE SOLVATES

The present invention relates to macrolide solvates, i.e. solvates of azithromycin and similar compounds. Azithromycin (9-deoxo-9a-aza-9a-methyl-9a-homoerythromycin A) is a well-known antibacterial agent, described e.g. Ib. The Merck Index, $12^{th}$ edition (1996), page 157 (item 946) and may be produced according to a known process. Azithromycin may be obtained in the form of a solvate, e.g. in the form of a hydrate, such as a monohydrate or e.g. in the form of a dihydrate. It is known that azithromycin in the form of a monohydrate may be unstable and may contain degradation products, when set out to normal air humidity conditions and azithromycin in the form of a monohydrate produced according to known methods, e.g. by precipitation with water from an ethanolic solution, may beside its instability contain a high content of residual solvents. Thus, azithromycin currently on the market is in the form of a dehydrate which is known to be stable under normal air humidity conditions.

We have now surprisingly found that azithromycin may be obtained in the form of a, e.g. crystalline, monohydrate which is stable.

In one aspect the present invention provides azithromycin in the form of a monohydrate comprising from 4.0% to 6.5% w/w of water.

Azithromycin in the form of a monohydrate comprising from 4.0% to 6.5% w/w of water is hereinafter designated as "azithromycin according to the present invention".

Azithromycin according to the present invention contains water from 4.0% to 6.5%. The calculated amount of water in azithromycin in the form of a composition consisting of 1 mol of azithromycin and 1 mol of water is around 2.35% w/w, but an azithromycin/water composition wherein the water content is different from 2.35% w/w, does not necessarily mean that the crystallisation form of azithromycin is different from the crystallisation form of azithromycin in the form of a monohydrate. We have found that the X-ray powder diffraction pattern of azithromycin according to the present invention is corresponding to the X-ray powder diffraction pattern which is disclosed for azithromycin in the form of a monohydrate as disclosed in EP 941 999, FIG. 2, and EP 984 020, FIG. 2; and is substantially different from the X-ray powder diffraction pattern of azithromycin in the form of a dihydrate as disclosed in EP 941 999, FIG. 1, and in EP 984 020, FIG. 4. Azithromycin according to the present invention is substantially crystalline and maintains its X-ray powder diffraction pattern, i.e. it maintains its crystalline structure, within at least 2 weeks, e.g. up to 6 weeks and more, such as 2 to 6 weeks, under normal, e.g. normal air, humidity conditions, e.g. even at elevated temperatures.

Azithromycin according to the present Invention may be further defined by Its low content of azithromycin degradation products. E.g. we have found that in a sample of azithromycin according to the present invention practically no azithromycin degradation occurs, when setting out said sample to normal, e.g. normal air, humidity conditions, such as 70% to 80%, e.g. 75% humidity, within 2 to 6 weeks, e.g. within 6 weeks, and even longer, e.g. at elevated temperatures, such as temperatures above room temperatures, e.g. 35° C. to 45° C., such as 40° C.; e.g. we have found that the degradation of azithromycin according to the present invention under a temperature of 40° C. in an environment of 75% humidity within 6 weeks is less than 2.0%, even less than 1.0% and even less than 0.5%, namely (around) 0.1%, whereas azithromycin in the form of a monohydrate having a water content of 2.8% to 3.6% shows a degradation of 2.5% already within 2 weeks, which degradation is increasing within 4 weeks, and is of almost 7% within 6 weeks under the same conditions.

In another aspect the present invention provides azithromycin in the form of a monohydrate, characterized in that in a sample thereof the degradation of azithromycin is less than 2%, even less than 1.5%, such as 0.05% to 1.0%, e.g. 0.05 to 0.5%, when setting out said sample to normal, e.g. normal air, humidity conditions, such as 75% envionmental humidity, e.g. at elevated temperatures, such as of 40° C., within at least 2 weeks, e.g. within 2, e.g. 4, and e.g. even 6 weeks.

Azithromycin degradation which occurs under the above described conditions in a sample of azithromycin according to the present invention is within the percentage range of degradation products allowed by Pharmacopeiias in commercial azithromycin forms.

Azithromycin according to the present invention may be further defined by its stable water content. E.g. we have found that in a sample of azithromycin according to the present invention the water content practically does not increase, e.g. the water content remains essentially the same, when setting out said sample to normal, e.g. normal air, humidity conditions, such as 70% to 80%, e.g. 75% humidity, within 6 weeks, e.g. within 4 to 6 weeks, and even longer, e.g. at elevated temperatures, such as temperatures above room temperatures, e.g. 35° C. to 45° C., such as 40° C.; e.g. we have found that the water content of azithromycin according to the present invention at a temperature of 40° C., in an environment of 75% humidity remains substantially the same as in week 0 within 4 weeks and even 6 weeks.

In another aspect the present invention provides azithromycin in the form of a monohydrate, characterized in that in a sample thereof the water content remains substantially the same as in week 0, when setting out said sample to normal, e.g. normal air, humidity conditions, such as 75% envionmental humidity, e.g. at elevated temperatures, such as temperatures above room temperatures, e.g. 35° C. to 45° C., e.g. 40° C., for a period of 4 weeks, e.g. 4 to 6 weeks.

Azithromycin according to the present invention may be obtained e.g. as follows: Azithromycin in any form, e.g. in free base form; and in the form of a salt, e.g. in the form of a hydrochloride, e.g. a dihydrochloride, acetate; and/or in the form of a solvate, e.g. in the form of a monohydrate, having a water content which is different from 4.0% to 6.5%, in anhydrous form, or in the form of a dihydrate, preferably in the form of a salt, may be e.g. used as a starting material. A solution of azithromycin in the form of a salt in a solvent may be produced, e.g. either by dissolving azithromycin in the form of a salt in a solvent; or by conversion of azithromycin in free form in a solvent into azithromycin in the form of a salt; e.g. by addition of an acid to azithromycin in solvent. A "solution" includes a suspension, In which at least a part of azithromycin (e.g. in the form of a salt) is dissolved. Appropriate acids include organic acids, for example formic acid or acetic acid, and inorganic acids, for example hydrochloric, hydrobromic, nitric or sulphuric acid, preferably hydrochloric acid or sulphuric acid. Solvent includes solvent which is appropriate to dissolve azithromycin in the form of a salt, e.g. including aqueous solvent. Aqueous solvent includes water or a mixture of water with organic solvent, e.g. one or more organic solvents, for example water miscible and water immiscibl organic solvent, such as alcohols, e.g. methanol, ethanol, isopropanol; ketones such as acetone, methyl isobutyl ketone; alkyl carboxylic acid esters, e.g. (C$_{1-4}$)alkyl carboxylic acid esters, of formic or acetic acid, e.g. methyl acetate, ethyl acetate, isopropyl acetate, butyl acetate; aromatic hydrocarbons such as toluene, xylenes; ethers, such as tetrahydrofuran, methyl t.butyl ether; chlorinated hydrocarbons such as methylene chloride; and amides such as monoalkyl and dialkyl amides, e.g. N-methyl formamide, N,N-dimethylacetamide, N,N-dimethylformamide; preferably water or a mixture of water with one or more alcohols, ketones, alkyl acetates; e.g. water, or aqueous solvent, such as water or water containing 0.5% to 20% v/v; such as 1% to 15% v/v of organic solvent. It is one advantage of the present invention that water in the absence of organic solvent may be used.

Appropriate reaction conditions for the production of a solution of azithromycin in the form of a salt according to the process of the present invention include, e.g.

(i) A temperature at which azithromycin is not degraded, e.g. including a temperature range of –20° C. to 90° C., such as 0° C. to 70° C., (ii) An appropriate pressure, e.g. atmospheric pressure, and a pressure which is above or below atmospheric pressure;

(iii) Appropriate dilution, e.g. a dilution range of 1 g to 500 g of azithromycin in the form used as a starting material, per litre of solvent.

A resulting solution of azithromycin In the form of a salt in a solvent may be optionally purified as appropriate, e.g. by filtration, charcoal treatment; In order to remove impurities. The pH of an, e.g. purified, solution of azithromycin in the form of a salt may be adjusted to an pH where azithromycin is present in free form, including e.g. a pH of, e.g. ca., 8.0 to 13.0, such as 9.0 to 12.0, e.g. 10.0 to 11.0; e.g. by addition of a base to a solution of azithromycin in the form of a salt in a solvent. A "solution" of azithromycin in free form includes a suspension, in which at least a part of azithromycin is dissolved. Appropriate bases include bases which are suitable for pH adjustment, e.g. inorganic bases, such as ammonia or alkali-, e.g. sodium, potassium; earth alkali-, e.g. calcium-, magnesium-; and ammonium-hydroxide, -carbonate, -hydrogencarbonate; and organic bases, such as amines, e.g. alkyl amines; and a mixture of individual bases, e.g. individual bases as described above. A base is preferably a hydroxide, e.g. sodium, or ammonia; preferably in aqueous solution. Azithromycin in free form and in the form of a stable crystalline monohydrate may precipitate from the solution and may be isolated, e.g. analogously to a method as conventional, e.g. by centrifugation or filtration; and may be dried at appropriate temperatures, e.g. including a temperature range of 20° C. to 80° C., e.g. under atmospheric pressure or under vacuum; until a water content of 4.0% to 6.5% is achieved. Crystalline azithromycin in the form of a monohydrate may be obtained comprising from 4.0% to 6.5% of water.

In another aspect the present invention provides a process for the production of azithromycin in the form of a monohydrate comprising from 4.0% to 6.5% of water, said process comprising the steps (i) adjusting the pH of a solution of azithromycin in the form of a salt wherein the solvent is selected from water or a mixture of water and organic solvent, (ii) isolating azithromycin of formula I in the form of a monohydrate, and (iii) drying to obtain azithromycin in the form of a monohydrate comprising from 4.0% to 6.5% of water.

When solely water is used as a solvent azithromycin according to the present invention may be obtained, substantially free of organic solvent. Substantially free includes an analytically undetectable amount up to an analytically detectable amount of 0.5% w/w of organic solvent; which is an amount of organic solvents; which is within the range which European Pharmacopoellas define as appropriate for pharmaceutical ingredients, e.g. for solvents with low toxic potential (Class 3 solvents).

In another aspect the present invention provides azithromycin in the form of a crystalline monohydrate, which is substantially free of organic solvent.

Azithromycin according to the present invention, is useful in the production of a pharmaceutical composition comprising azithromycin as an active ingredient.

In another aspect the present invention provides a pharmaceutical composition, comprising, e.g. essentially consisting of, azithromycin according to the present invention in association with at least one pharmaceutical carrier or diluent.

A pharmaceutical composition according to the present invention may contain the same concentrations of azithromycin and may be used for the same indications in the same dosage ranges as a known pharmaceutical composition comprising azithromycin in the form of a dihydrate, e.g. as is currently on the market

EXAMPLES

In the following examples all temperatures are in degree Centigrade and are uncorrected. The X-ray powder diffraction pattern of azithromycin in the form of a monohydrate obtained according to the following example corresponds to that of azithromycin in the form of a monohydrate. Azithromycin in the form of a monohydrate obtained according to the following example maintains its crystallinity and its X-ray powder diffraction pattern and contains substantially no degration products when kept for 6 weeks under normal air humidity conditions at elevated temperatures. Water content (% w/w) is determined by the K. Fischer Example To a suspension of 20 g of azithromycin in 83 ml of water, HCl is added until dissolution occurs. The solution obtained is filtrated, in order to remove undissolved particles, and the filtrate obtained is added dropwise to 103 ml of water whilst adjusting the pH to 10 to 11 by addition of 20% NaOH at a temperature of ca. 55° C. A solid precipitates, is filtrated off, washed and dried until a water content of 4.0 to 6.5% is achieved. 18.4 g of azithromycin in the form of a monohydrate in crystalline form are obtained. Water content: 6.0% Water content after 2 days at room temperature under normal air humidity conditions: 6.3% Water content after 13 days at room temperature under normal air humidity conditions: 6.3%

The X-ray diffraction powder pattern of azithromycin obtained corresponds to the X-ray diffraction powder pattern of azithromycin in the form of a monohydrate as disclosed In EP 941 999, FIG. 2, and EP 984 020, FIG. 2 on day 1, on day 2 and on day 13.

Stability and Comparison Example

Samples of Azithromycin in the Form of a Monohydrate Comprising 5.3% of water, and 2.8% of water are set out for 6 weeks to an environment having a relative humidity of 75% at a temperature of 400. Potency (content) of azithromycin, azithromycin degradation and water content in the samples are determined in week 0, week 2, week 4 and week 6. Potency and degradation are determined on azithromycin anhydrous basis by HPLC. The water content is determined by the Karl Fischer method.

Results are Obtained for azithromycin comprising 5.3% of water as set out in TABLE 1 below,
for azithromycin comprising 2.8% of water as set out in TABLE 2 below:

TABLE 1

| WEEK | POTENCY (%) | Degradation (%) | WATER (%) |
|---|---|---|---|
| 0 | 99.8 | — | 5.3 |
| 2 | 98.9 | 0.1 | 5.3 |
| 4 | 99.5 | 0.1 | 5.3 |
| 6 | 99.5 | 0.1 | 5.3 |

TABLE 2

| WEEK | POTENCY (%) | DEGRADATION (%) | WATER (%) |
|---|---|---|---|
| 0 | 99.7 | — | 2.8 |
| 2 | NO CONTROL | 2.5 | 2.8 |
| 4 | NO CONTROL | 6.1 | 3.3 |
| 6 | 91.6 | 6.6 | 3.6 |

In TABLE 1 and TABLE 2

Crystalline azithromycin in both samples shows a X-ray powder diffraction pattern corresponding to that of azithromycin in the form of a monohydrate according to EP 941 999, FIG. 2, and EP 984 020, FIG. 2, in week 0 and in week 6.

The potency of azithromycin in % of each sample within the corresponding time period is set out in TABLE 1 and TABLE 2 under "Potency (%)".

The degradation of azithromycin in % of each sample within the corresponding time period is set out in TABLE 1 and TABLE 2 under "Degradation (%).

The water content in % of each sample within the corresponding time period is indicated in TABLE 1 and TABLE 2 under "Water (%)".

What is claimed is:

1. Azithromycin in the form of a monohydrate comprising from 4.0% to 6.5% w/w of water.

2. Azithromycin in the form of a monohydrate, characterized in that in a sample thereof the degradation of azithromycin is less than 2% when setting out said sample to normal humidity conditions at temperatures above room temperature, within at least 2 weeks.

3. Azithromycin in the form of a monohydrate, characterized in that in a sample thereof the water content remains substantially the same as in week 0, when setting out said sample to normal humidity conditions at temperatures above room temperature for a period of 4 weeks.

4. A pharmaceutical composition comprising azithromycin according to claim 1 and at least one pharmaceutical carrier or diluent.

5. A process for the production of azithromycin in the form of a monohydrate comprising from 4.0% to 6.5% of water, said process comprising the steps (i) adjusting the pH of a solution of azithromycin in the form of a salt wherein the solvent is selected from water, (ii) isolating azithromycin in the form of a monohydrate, and (iii) drying to obtain azithromycin in the form of a monohydrate comprising from 4.0% to 6.5% of water.

6. A composition according to claim 2 wherein said temperatures above room temperature are from 35° C. to 45° C.

7. A composition according to claim 3 wherein said temperatures above room temperature are from 35° C. to 45° C.

* * * * *

UNITED STATES PATENT AND TRADEMARK OFFICE
CERTIFICATE OF CORRECTION

PATENT NO. : 6,949,519 B2
DATED : September 27, 2005
INVENTOR(S) : Centellas et al.

It is certified that error appears in the above-identified patent and that said Letters Patent is hereby corrected as shown below:

Title page,
Item [60], Related U.S. Application Data, should read -- Claims benefit of 60/253,119 filed November 27, 2000 --.

Signed and Sealed this

Seventh Day of February, 2006

JON W. DUDAS
*Director of the United States Patent and Trademark Office*